United States Patent

Fuchs et al.

[11] Patent Number: 5,886,181
[45] Date of Patent: Mar. 23, 1999

[54] PROCESS FOR THE PREPARATION OF OPTICALLY ACTIVE PIPERAZINE-2-CARBOXYLIC ACID DERIVATIVES

[75] Inventors: Rudolf Fuchs, Sion; Jean-Paul Roduit, Grône, both of Switzerland

[73] Assignee: Lonza, Ltd., Gampel/Valais, Switzerland

[21] Appl. No.: 651,260

[22] Filed: May 23, 1996

[30] Foreign Application Priority Data

May 23, 1995 [CH] Switzerland ............................. 1520/95
Dec. 19, 1995 [CH] Switzerland ............................. 3581/95

[51] Int. Cl.[6] ........................ C07D 241/04; C07D 413/06
[52] U.S. Cl. ........................ 544/388; 544/387; 544/389; 544/390; 544/121
[58] Field of Search ................................... 544/387, 388, 544/389, 390, 121

[56] References Cited

U.S. PATENT DOCUMENTS

| | | | |
|---|---|---|---|
| 5,011,995 | 4/1991 | Pugin et al. | 564/302 |
| 5,371,256 | 12/1994 | Togni et al. | 556/14 |
| 5,463,067 | 10/1995 | Askin et al. | 548/113 |
| 5,463,097 | 10/1995 | Togni et al. | 556/14 |
| 5,466,844 | 11/1995 | Spindler et al. | 556/11 |
| 5,491,238 | 2/1996 | Askin et al. | 546/270 |
| 5,496,948 | 3/1996 | Askin et al. | 544/368 |
| 5,563,308 | 10/1996 | Spindler et al. | 585/277 |
| 5,563,309 | 10/1996 | Togni et al. | 585/277 |
| 5,565,594 | 10/1996 | Spindler et al. | 556/28 |
| 5,583,241 | 12/1996 | Spindler | 556/11 |
| 5,618,939 | 4/1997 | Askin et al. | 544/368 |
| 5,637,711 | 6/1997 | Askin et al. | 544/374 |
| 5,723,615 | 3/1998 | Rossen et al. | 544/388 |

FOREIGN PATENT DOCUMENTS

| | | |
|---|---|---|
| 0175364 | 3/1986 | European Pat. Off. . |
| 0302021 | 2/1989 | European Pat. Off. . |
| 0541168 | 5/1993 | European Pat. Off. . |
| 0564406 | 10/1993 | European Pat. Off. . |
| 0612758 | 8/1994 | European Pat. Off. . |
| 0646590 | 4/1995 | European Pat. Off. . |
| WO 95/02583 | 1/1995 | WIPO . |
| WO 95/02584 | 1/1995 | WIPO . |

OTHER PUBLICATIONS

Rossen et al, *Tetrahedron Letters 36*, pp. 6419–6422 (Sep. 4, 1995).
Kandzia et al, *Chemical Abstracts*, vol. 125, No. 142774 (1996) (Abstract for DE 4,446,025 Jun. 27, 1996).
*Patent Abstracts of Japan*, vol. 13, No. 339 (C–624), [3687], (Jul. 31, 1989), Yasuo et al.
E. Felder et al., "Über die katalytische . . . ", Helv. Chim. Acta, vol. 43, (1960), pp. 888–896.
T. Hayashi et al., "Optically Active Ruthenocenylbis(phosphines) . . . ", J. Am. Chem. Soc., (1994), 116, 4221–4226.
T. Hayashi et al., "Asymmetric Synthesis . . . ", Bull. Chem. Soc. Jpn., (1980), 53, 1138–1151.
J.C. Sheehan et al., J. AM. Chem. Soc., (1958), 80, 1154.

*Primary Examiner*—Emily Bernhardt
*Attorney, Agent, or Firm*—Fisher,Christen&Sabol

[57] ABSTRACT

Optically active piperazine-2-carboxylic acid derivatives of the general formula:

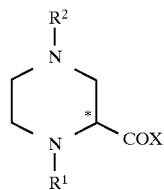

wherein $R^1$ and $R^2$ are inter alia hydrogen, alkyl or acyl and X is alkoxy or a (substituted) amino group, are prepared by asymmetric hydrogenation of the corresponding 1,4,5,6-tetrahydropyrazines, catalyzed by optically active rhodium, ruthenium or iridium complexes. The compounds of the Formula 1 are intermediates for the preparation of pharmaceutical active ingredients, for example, HIV protease inhibitors.

25 Claims, No Drawings

PROCESS FOR THE PREPARATION OF OPTICALLY ACTIVE PIPERAZINE-2-CARBOXYLIC ACID DERIVATIVES

FIELD OF THE INVENTION

The present invention relates to a process for the preparation of novel and known optically active piperazine-2-carboxylic acid derivatives, especially esters and amides of (R)- or (S)-piperazine-2-carboxylic acid, which optionally carry substituents on the ring nitrogen atoms, and are represented by the general formula:

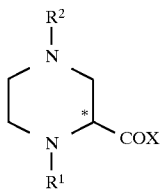

I wherein $R^1$ and $R^2$ independently of one another are each hydrogen, $C_{1-4}$-alkyl, optionally substituted $C_{1-6}$-alkanoyl, $C_{2-6}$-perfluoroalkanoyl, aroyl, arylalkyl, $C_{1-6}$-alkoxycarbonyl, aryloxycarbonyl, carbamoyl or an amino-protecting group, and X is a hydroxyl group, a $C_{1-6}$-alkoxy group or a group of the formula —$NR^3R^4$, wherein (i) $R^3$ and $R^4$ independently of one another are hydrogen, $C_{1-6}$-alkyl, $C_{3-6}$-cycloalkyl, aryl or an amino-protecting group, or (ii) $R^3$ and $R^4$, together with the nitrogen atom, form an optionally substituted 5- or 6-membered saturated heterocyclic ring, or (iii) $R^3$ is hydrogen and $R^4$ is a group of the formula:

wherein $R^6$ is hydrogen, $C_{1-4}$-alkyl or aryl and $R^5$ is hydrogen or the side-group of an amino acid, by asymmetric hydrogenation of the corresponding 1,4,5,6-tetrahydropyrazine-2-carboxylic acid derivatives in the presence of optically active rhodium, ruthenium or iridium complexes.

Compounds of this group are valuable intermediates, especially for the preparation of pharmaceutical active ingredients. Thus, for example, some known compounds in which X=NH-t-Bu and which have the (S) configuration are structural units for HIV protease inhibitors (European Published Patent Application No. A 541,168).

The invention further relates to novel 1,4,5,6-tetrahydropyrazine-2-carboxylic acid derivatives as starting materials for the asymmetric hydrogenation and to a process for their preparation.

Here and in the following text $C_{1-n}$-alkyl is always to be understood as meaning linear or branched primary, secondary or tertiary alkyl groups having 1 to n carbon atoms, for example, $C_{1-6}$-alkyl is to be understood as meaning groups such as methyl, ethyl, propyl, butyl, pentyl, hexyl, isopropyl, isobutyl, tert-butyl, isopentyl or neopentyl. Likewise, $C_{1-n}$-alkoxy and $C_{1-n}$-alkoxycarbonyl are to be understood as meaning the groups made up of $C_{1-n}$-alkyl and oxygen or oxygen and carbonyl. Optionally substituted $C_{1-n}$-alkanoyl ($C_{1-n}$-acyl) is to be understood as meaning linear or branched alkanoyl groups having 1 to n carbon atoms (including carbonyl carbon) which can also carry substituents such as $C_{1-4}$-alkoxy groups; for example, $C_{1-6}$-alkanoyl is to be understood as meaning groups such as formyl, acetyl, methoxyacetyl, propionyl, butyryl, isobutyryl, valeryl or caproyl. Analogously $C_{2-n}$-perfluoroalkanoyl is to be understood as meaning the corresponding perfluorinated acyl groups such as trifluoroacetyl or pentafluoropropionyl. Arylalkyl is to be understood especially as meaning groups such as benzyl or phenethyl, aryl is to be understood especially as meaning phenyl or substituted phenyl, and aroyl is to be understood especially as meaning benzoyl or substituted benzoyl. $C_{3-6}$-cycloalkyl is to be understood as meaning cyclopropyl, cyclobutyl, cyclopentyl or cyclohexyl. Amino-protecting groups are to be understood as meaning the protecting groups conventionally used in peptide chemistry, for example, benzyloxycarbonyl (Z) or tert-butoxycarbonyl (Boc). The expression "saturated heterocyclic ring" also covers rings with several heteroatoms, or optionally several different heteroatoms, such as morpholine. The expression "side-groups of an amino acid" is to be understood as meaning the radicals denoted by R in the general amino acid formula R—CH(NH$_2$)—COOH, especially those of the natural amino acids.

BACKGROUND ART

Hitherto known syntheses of compounds of the Formula I are based on the parent compound ($R^1=R^2=H$, X=OH), which can be obtained in optically active form by classical resolution of the racemate [E. Felder et al., *Helv. Chim. Acta*, (1960), 43, 888–896]. First the ring nitrogen atoms are protected and then the free carboxyl group is converted to the amide. At best the process is suitable for the laboratory scale and it requires the use of expensive reagents.

BROAD DESCRIPTION OF THE INVENTION

The main object of the present invention is to provide a process which can also be carried out on the industrial scale and which does not necessitate resolution of the racemate. Other objects and advantages of the invention are set out herein or are obvious herefrom to one skilled in the art.

The objects and advantages of the invention are achieved by the processes and compounds of the invention.

The invention involves a process for the preparation of optically active piperazine-2-carboxylic acid derivatives of the general formula:

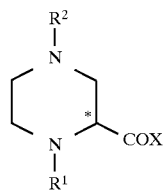

I wherein $R^1$ and $R^2$ independently of one another are each hydrogen, $C_{1-4}$-alkyl, optionally substituted $C_{1-6}$-alkanoyl, $C_{2-6}$-perfluoroalkanoyl, aroyl, arylalkyl, $C_{1-6}$-alkoxycarbonyl, aryloxylcarbonyl, carbamoyl or an amino-protecting group, and X is a hydroxyl group, a $C_{1-6}$-alkoxy group or a group of the formula —$NR^3R^4$, wherein (i) $R^3$ and $R^4$ independently of one another are hydrogen, $C_{1-6}$-alkyl, $C_{3-6}$-cycloalkyl, aryl or an amino-protecting group, or (ii) $R^3$ and $R^4$, together with the nitrogen atom, form an optionally substituted 5- or 6-membered saturated heterocyclic ring, or (iii) $R^3$ is hydrogen and $R^4$ is a group of the formula

wherein $R^6$ is hydrogen, $C_{1-4}$-alkyl or aryl and $R^5$ is hydrogen or the side-group of an amino acid. In the process, a corresponding 1,4,5,6-tetrahydropyrazine-2-carboxylic acid derivative of the general formula:

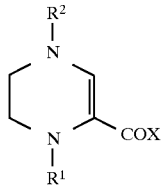

II wherein $R^1$, $R^2$ and X are as defined above, is asymmetrically hydrogenated in the presence of a catalytically active, optically active rhodium, ruthenium or iridium complex.

The invention also involves optically active piperazine-2-carboxylic acid derivatives of the general formula:

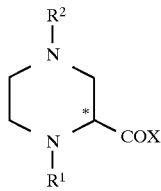

I wherein $R^1$ is $C_{1-6}$-alkanoyl or $C_{2-6}$-perfluoroalkanoyl and $R^2$ and X are as defined above, and mixtures of their enantiomers.

The invention also involves 1,4,5,6-tetrahydropyrazine-2-carboxylic acid derivatives of the general formula:

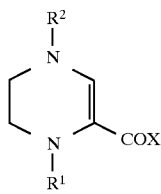

II wherein $R^1$, $R^2$ and X are as defined above, with the proviso that $R^1$ and $R^2$ are not simultaneously hydrogen.

The invention further involves a process for the preparation of the above-defined 1,4,5,6-tetrahydropyrazine-2-carboxylic acid derivatives. In the process, a pyrazinecarboxylic acid derivative of the general formula:

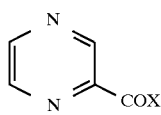

VI wherein X is as defined above, is hydrogenated with hydrogen on a palladium catalyst to give the 1,4,5,6-tetrahydropyrazine-2-carboxylic acid derivative of the general formula:

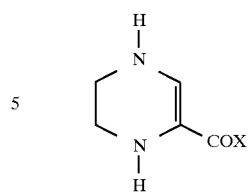

VII and the latter is then converted by a known method to the compound substituted on $N^1$ and/or $N^4$.

DETAILED DESCRIPTION OF THE INVENTION

It has been found that the 1,4,5,6-tetrahydropyrazine-2-carboxylic acid derivatives corresponding to the target compounds, of the general formula:

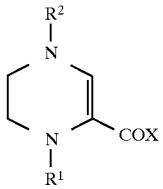

II wherein $R^1$, $R^2$ and X are as defined above, can be asymmetrically hydrogenated to the target compounds with hydrogen in the presence of catalytically active, optically active rhodium, ruthenium or iridium complexes.

It is preferable to use 1,4,5,6-tetrahydropyrazine-2-carboxylic acid derivatives in which $R^1$ and/or $R^2$ are each $C_{1-6}$-alkanoyl, $C_{2-6}$-perfluoroalkanoyl, tert-butoxycarbonyl ("Boc") or benzyloxycarbonyl ("Z"). It is very particularly preferable to use 1,4,5,6-tetrahydropyrazine-2-carboxylic acid derivatives in which $R^1$ and/or $R^2$ are each formyl or trifluoroacetyl; these derivatives have the advantage that the substituents $R^1$ and $R^2$ can optionally be cleaved selectively, i.e., the formyl group under acid conditions and the trifluoroacetyl group under basic conditions. It is also preferable to use 1,4,5,6-tetrahydropyrazine-2-carboxylic acid amide derivatives in which X is a group of the formula $—NR^3R^4$, with $R^3$ and $R^4$ being as defined above. Particularly preferred amides are those in which $R^3$ is hydrogen and $R^4$ is a $C_{1-6}$-alkyl group, especially a tert-butyl group.

The catalytically active, optically active rhodium, ruthenium or iridium complex used is preferably a rhodium complex formed by reaction of an Rh(I) complex with an optically active metallocenylphosphine.

The optically active metallocenylphosphines used are preferably compounds of the general formula:

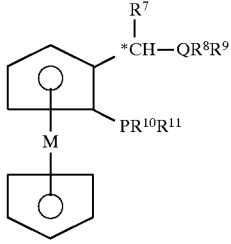

III wherein M is iron(II) or ruthenium(II), Q is nitrogen or phosphorus, $R^7$ is a $C_{1-4}$-alkyl group and $R^8$ to $R^{11}$ independently of one another are each $C_{1-8}$-alkyl, $C_{5-8}$-cycloalkyl, phenyl or substituted phenyl. Particularly preferred metallocenylphosphines are those in which M is iron, i.e., the ferrocenylphosphines. Other particularly preferred metallocenylphosphines are those in which Q is phosphorus, i.e., metallocenyldiphosphines. Other particularly preferred metallocenylphosphines are those in which $R^7$ is methyl and $R^8$ and $R^9$ are identical and are tert-butyl or cyclohexyl. These last-mentioned metallocenylphosphines include, for example, 1-[1-(di-tert-butylphosphino)ethyl]-2-(diphenylphosphino)ferrocene and 1-[1-(dicyclohexylphosphino)ethyl]-2-(diphenylphosphino)-ferrocene. The preparation of these compounds is described in European Published Patent Application No. 0,564,406 or U.S. Pat. No. 5,371,256. Other optically active metallocenylphosphines are described in, for example, T. Hayashi et al., *J. Am. Chem. Soc.*, (1994), 116, 4221 to 4226, European Published Patent Application No. 0,612,758 or U.S. Pat. No. 5,466,844 and T. Hayashi et al., *Bull. Chem. Soc. Jpn.*, (1980), 53, 1138 to 1151.

As Rh(I) complexes which, together with the optically active metallocenylphosphines, form the catalytically active, optically active rhodium complexes, it is preferable to use neutral dinuclear complexes of the general formula:

$$[Rh(L)A]_2 \quad\quad IV$$

wherein L is one $C_{4-12}$-diene or two $C_{2-12}$-alkene molecules and A is chlorine, bromine or iodine, preferably chlorine or bromine.

Other preferred Rh(I) complexes are those of the general formula:

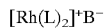

$$[Rh(L)_2]^+B^- \quad\quad V$$

wherein L is as defined above and $B^-$ is the anion of an oxo acid or a complex acid. Anions of oxo acids are to be understood as meaning, for example, anions such as $ClO_4^-$, $SO_3F^-$, $CH_3SO_3^-$, or $CF_3SO_3^-$, and anions of complex acids are to be understood as meaning, for example, $BF_4^-$, $PF_6^-$, $AsF_6^-$, $SbF_6^-$ or $SbCl_6^-$.

Particularly preferred ligands L in the Rh(I) complexes IV and V are dienes, especially nonbornadiene and 1,5-cyclooctadiene.

These complexes are known, for example, from European Published Patent Application No. 0,302,021 or U.S. Pat. No. 5,011,995, which is incorporated herein by reference.

The asymmetric hydrogenation of the 1,4,5,6-tetrahydropyrazine-carboxylic acid derivatives II is advantageously carried out at a temperature of 20° to 200° C. and a hydrogen pressure of 1 to 200 bar. The molar ratio of catalyst to educt is advantageously 1:100 to 1:5000, preferably 1:1000 to 1:2000.

Examples of suitable solvents for the asymmetric hydrogenation are water, lower alcohols such as methanol, aromatic hydrocarbons such as toluene, ketones such as acetone, or carboxylic acid esters such as ethyl acetate.

The optically active piperazine-2-carboxylic acid derivatives I in which one of the two substituents $R^1$ and $R^2$ is $C_{1-6}$-alkanoyl or $C_{2-6}$-perfluoroalkanoyl and the other substituent and X are as defined above are a further subject of the present invention, both as such and in the form of mixtures of their enantiomers. Mixtures of enantiomers are to be understood here as meaning especially mixtures in which one enantiomer is enriched relative to the other. Particularly preferred compounds are those in which $R^1$ is trifluoroacetyl and/or $R^2$ is formyl.

The 1,4,5,6-tetrahydropyrazinecarboxylic acid derivatives II are novel compounds and are a further subject of the present invention. They can be prepared, for example, by partially hydrogenating a corresponding pyrazinecarboxylic acid derivative of the general formula:

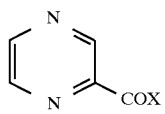

wherein X is as defined above, with hydrogen on a palladium catalyst to give the 1,4,5,6-tetrahydropyrazine-2-carboxylic acid derivative of the general formula:

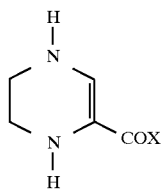

wherein X is as defined above, and then converting the latter by a known method, for example, by acylation with a carboxylic anhydride, to the compound substituted on the ring nitrogens $N^1$ and/or $N^4$.

Compound II in which X is a (substituted) amino group can also be prepared from 1,4,5,6-tetrahydropyrazine-2-carbonitrile, for example, by means of a Ritter reaction. The last-mentioned compound is readily obtainable by a process described in European Published Patent Application No. 0,175,364.

The Examples which follow clarify the implementation of the process according to the invention and the preparation of the compounds according to the invention without thereby implying a limitation.

EXAMPLE 1
Methyl pyrazinecarboxylate 106.6 g of thionyl chloride was added dropwise over 1 hour to 1200 ml of methanol under argon at 4° to 6° C. 100.1 g of pyrazinecarboxylic acid was added at 9° C. and the mixture was heated at 61° C. for 2 hours, the acid passing completely into solution. After cooling to room temperature, a solution of 145 g of sodium hydrogen carbonate in 1.4 l of water was added slowly. The methanol was distilled off on a rotary evaporator at a bath temperature of 45° C. and at 50 to 120 mbar and the residue was extracted three times with dichloromethane (400 ml, 100 ml, 100 ml). Concentration of the organic phase gave 83.15 g of crude product, which was recrystallized from ca. 250 g of diisopropyl ether. The yield of the title compound was 70.6 g plus 10.28 g from the mother liquor (total 72.5 percent). Further data concerning the title compound was:

| $^1$H NMR (CDCl$_3$, 400MHz): δ = | 4.05(s, 3H); |
|---|---|
| | 8.75(d, J=0.5Hz, 1H); |
| | 8.80(d, J=0.5Hz, 1H); |
| | 9.30(s, 1H). |

EXAMPLE 2
Methyl 1,4,5,6-tetrahydropyrazine-2-carboxylate 100 ml of methyl acetate, 7.8 g of methyl pyrazinecarboxylate (prepared according to Example 1) and 1.5 g of palladium on activated charcoal (10% Pd) were placed in a 500 ml autoclave. The autoclave was flushed twice with nitrogen and twice with hydrogen, the gas being introduced under a pressure of up to 8 bar and allowed to expand again. Hydrogenation was then carried out for 9 hours at 20° C. and a hydrogen pressure of 10 bar, with stirring. The autoclave was then flushed with nitrogen, the reaction mixture was filtered on a suction filter (0.45 μm pore width) and the catalyst was washed with methyl acetate. Crude methyl 1,4,5,6-tetrahydropyrazine-2-carboxylate was obtained by concentration. Other data concerning the title compound was:

| ¹H NMR(CDCl₃, 400MHz): δ = | 3.17 to 3.25(m, 2H); |
| --- | --- |
| | 3.33 to 3.42(m, 2H); |
| | 3.71(s, 3H); |
| | 6.93(bs, 1H). |

The product was acylated without further purification.

EXAMPLE 3
Methyl 1-acetyl-1,4,5,6-tetrahydropyrazine-2-carboxylate 15.10 g (192.5 mmol) of acetyl chloride was added dropwise over 25 minutes to 25.00 g (175.9 mmol) of methyl 1,4,5,6-tetrahydropyrazine-2-carboxylate, 250 ml of tetrahydrofuran and 21.30 g (210.5 mmol) of triethylamine at 0° C. The mixture was then heated to room temperature and, after 1 hour, 200 ml of ethyl acetate were added. The aqueous phase was washed a further 3 to 4 times with a total of 500 ml of ethyl acetate and the combined organic extracts were dried over magnesium sulfate. After the solvent had been stripped off, 22.30 g (69%) of the title compound were obtained as a yellow oil. Recrystallization from ethyl acetate gave methyl 1-acetyl-1,4,5,6-tetrahydropyrazine-2-carboxylate in the form of a light yellow, crystalline solid. The melting point of the title compound was: 136° to 139° C. Other data concerning the title compound was:

| ¹H NMR(CDCl₃, 400MHz): δ = | 2.10(s, 2H); |
| --- | --- |
| | 3.35(bs, 2H); |
| | 3.00 to 5.00(bm, 2H); |
| | 3.75(s, 3H); |
| | 5.02(bs, 1H); |
| | 7.32(d, 1H). |

EXAMPLE 4
Methyl 1,4-diacetyl-1,4,5,6-tetrahydropyrazine-2-carboxylate 10.1 g of methyl 1,4,5,6-tetrahydropyrazine-2-carboxylate in 200 g of acetic anhydride were heated for 2 hours at 135° C. The excess acetic anhydride was then distilled off at 57° C./55 mbar. 100 g of dichloromethane and 20 g of water were added to the residue. The organic phase was separated off, washed with 30 ml of water and concentrated to dryness to give 18.1 g of crude product as an oily residue. This was purified by medium pressure column chromatography (column 5×40 cm, silica gel) with ethyl acetate/dichloromethane/methanol (10:5:1). The yield was 11.6 g (85%). Other data concerning the title compound was:

| ¹H NMR(DMSO-d₆, 80° C., 400MHz): δ = | 1.98(s, 3H); |
| --- | --- |
| | 2.25(s, 3H); |
| | 3.60 to 3.70(m, 1H); |
| | 3.70(s, 3H); |
| | 7.60(bd, 1H). |

EXAMPLE 5
1-Acetyl-1,4,5,6-tetrahydropyrazine-2-carboxylic acid tert-butylamide 70 g (0.77 mmol) of methanesulfonic acid was added slowly to 100 ml (1.75 mol) of acetic acid at room temperature, followed by 20.0 g (184 mmol) of 1,4,5,6-tetrahydropyrazine-2-carbonitrile. 23.0 g (410 mmol) of isobutane were introduced into this mixture at 25° C. and the resulting mixture was stirred for 5 hours. This was then neutralized with 30% sodium hydroxide solution, the temperature always being kept below 30° C. The mixture was adjusted to pH 8–10 and extracted with three times 200 ml of methyl ethyl ketone. The combined organic phases were dried over magnesium sulfate and the solvent was distilled off. The residue (41.2 g) was dissolved in 80 ml of ethyl acetate, with heating. After cooling to 20° C., 500 ml of hexane was added, the mixture was cooled further to 0° C. and, after 1 hour, the precipitated product was filtered off and dried. The yield was 32.6 g (79%) of light beige powder. The melting point of the title compound was: 151.3° to 152.6° C. Other data concerning the product was:

| ¹H NMR(CDCl₃, 400MHz): δ = | 2.08(s, 3H); |
| --- | --- |
| | 3.35(bs, 2H); |
| | 3.74(s, 3H); |
| | 2.00 to 5.00(bm, 2H); |
| | 7.31(d, J=7.0Hz, 1H). |
| ¹³C NMR(CDCl₃, 100MHz): δ = | 22.38(CH₃); |
| | 37.28(CH₂); |
| | 42.79(CH₂); |
| | 51.15(OCH₃); |
| | 103.63(C=); |
| | 135.94(CH=); |
| | 165.21(COO); |
| | 171.85(CON). |

EXAMPLE 6

1-Propionyl-1,4,5,6-tetrahydropyrazine-2-carboxylic acid tert-butylamide

The compound was prepared analogously to Example 5 using propionic acid instead of acetic acid. The yield was 75 percent. The melting point of the title compound was: 172.4° to 172.6° C. Other data concerning the title compound was:

| ¹H NMR(CDCl₃, 400MHz): δ = | 1.09(t, J=7.3Hz, 3H); |
| --- | --- |
| | 1.37(s, 9H); |
| | 2.39(q, J=7.3Hz, 2H); |
| | 3.28(m, 2H); |
| | 3.57(m, 2H); |
| | 5.41(bs, 1H); |
| | 5.49(bs, 1H); |
| | 7.09(d, J=6.3Hz, 1H). |
| ¹³C NMR(CDCl₃, 100MHz): δ = | 9.44(CH₃); |
| | 27.55(CH₂); |
| | 29.12(CH₃); |
| | 38.29(CH₂); |
| | 42.19(CH₂); |
| | 50.92(C); |
| | 106.66(C); |
| | 132.20(CH); |
| | 165.21(C=O); |
| | 177.20(C=O). |

EXAMPLE 7

1-isobutyryl-1,4,5,6-tetrahydropyrazine-2-carboxylic acid tert-butylamide

The compound was prepared analogously to Example 5 using isobutyric acid instead of acetic acid. The yield was 48 percent. The melting point of the title compound was: 180.0° to 184.4° C. Other data concerning the title compound was:

| | |
|---|---|
| ¹H NMR (CDCl₃, 400 MHz): δ = | 1.07 (d, J = 6.5 Hz, 6H), |
| | 1.37 (s, 9H); |
| | 2.82 (sept, J = 6.5 Hz 1H); |
| | 3.27 (m, 2H); |
| | 3.6 (bm, 2H); |
| | 4.94 (bs, 1H); |
| | 5.48 (bs, 1H); |
| | 7.12 (d, J = 6.3 Hz, 1H). |
| ¹³C NMR (CDCl₃, 100 MHz): δ = | 19.36 (CH₃); |
| | 29.07 (CH₃); |
| | 32.50 (CH); |
| | 38.39 (CH₂); |
| | 42.42 (CH₂); |
| | 50.94 (C); |
| | 106.73 (C); |
| | 132.07 (CH); |
| | 165.21 (C = 0); |
| | 180 85 (C = 0). |

EXAMPLE 8

1,4-Diacetyl-1,4,5,6-tetrahydropyrazine-2-carboxylic acid tert-butylamide 16.7 g (163 mmol) of acetic anhydride and 12.4 g (157 mmol) of pyridine were added to 20.00 g (88.8 mmol) of 1-acetyl-1,4,5,6-tetrahydropyrazine-2-carboxylic acid tert-butylamide and the mixture was stirred for 4 hours at 25° C. 100 ml of water was then added and the pH was adjusted to 6 with 30 ml of sodium hydroxide solution (20%). Extraction was then carried out by shaking with three times 100 ml of methyl ethyl ketone. The combined organic extracts were dried over magnesium sulfate, toluene was added and the mixture was concentrated. The vigorously foaming crude product crystallized and 11.40 g (48%) of the title compound was isolated in the form of a light brown solid. The melting point of the title compound was: 138.0° to 139.2° C. Other data concerning the title compound was:

| | |
|---|---|
| ¹H NMR (CDCl₃, 400 MHZ): δ = | 1.41 (s, 9H); |
| | 2.14 (s, 3H); |
| | 2.32 (s, 3H); |
| | 3.71 to 3.80 (m, 4H); |
| | 5.82 (bs, 1H); |
| | 7.34 (s, 1H). |
| ¹³C NMR (CDCl₃, 100 MHZ): δ = | 21.30 (CH₃); |
| | 21.58 (CH₃); |
| | 28.76 (CH₃); |
| | 39.44 (CH₂); |
| | 42.43 (CH₂); |
| | 51.76 (C); |
| | 116.61 (C); |
| | 123.36 (CH); |
| | 163.04 (C = 0); |
| | 168.56 (C = 0); |
| | 171.68 (C = 0). |

EXAMPLE 9

4-Acetyl-1-propionyl-1,4,5,6-tetrahydropyrazine-2-carboxylic acid tert-butylamide 168.7 g (0.705 mol) of 1-propionyl-1,4,5,6-tetrahydropyrazine-2-carboxylic acid tert-butylamide was placed in 1.92 l of a butyl acetate/acetonitrile mixture (4:1). The suspension was heated to 50° C. and 68.2 g (0.812 mol) of sodium hydrogen carbonate was added. A solution of 57.0 g (0.726 mol) of acetyl chloride in 120 ml of butyl acetate was added dropwise over 30 minutes. The reaction mixture was then stirred for a further 40 minutes at 50° C. 190 ml of water was added cautiously and the aqueous phase was separated off and re-extracted with 200 ml of butyl acetate at 50° C. The combined organic extracts were concentrated to 1100 ml and cooled slowly to 2° C. to induce crystallization. The solid was filtered off and rewashed with 100 ml of cold butyl acetate. Recrystallization from 700 ml of butyl acetate gave 183.8 g (92.7%) of the title compound in the form of white crystals. The melting point of the title compound was: 133.5° to 134.6° C. Other data concerning the title compound was:

| | |
|---|---|
| ¹H NMR (CDCl₃, 400 MHz): δ = | 1.13 (t, J = 7.3 Hz, 3H); |
| | 1.40 (s, 9H); |
| | 2.32 (s, 3H); |
| | 2.38 (q, J = 7.3 Hz, 2H); |
| | 3.70 (m, 4H); |
| | 5.77 (bs, 1H); |
| | 7.34 (s, 1H). |
| ¹³C NMR (CDCl₃, 100 MHz): δ = | 9.27 (CH₃); |
| | 21.46 (CH₃); |
| | 27.88 (CH₂); |
| | 28.75 (CH₃); |
| | 39.88 (CH₂); |
| | 42.55 (CH₂); |
| | 51.72 (C); |
| | 116.49 (C); |
| | 123.43 (CH); |
| | 163.20 (C = 0); |
| | 168.61 (C = 0); |
| | 175.6 (C = 0). |

EXAMPLE 10

1-Acetyl4-benzoyl-1,4,5,6-tetrahydropyrazine-2-carboxylic acid tert-butylamide

Analogously to Example 9, the title compound was obtained in the form of a white crystalline solid from 1-acetyl-1,4,5,6-tetrahydropyrazine-2-carboxylic acid tert-butylamide and benzoyl chloride. The melting point of the title compound was: 157.0° to 157.5° C. Other data concerning the title compound was:

| | |
|---|---|
| ¹H NMR (CDCl₃, 400 MHz): δ = | 1.37 (s, 9H); |
| | 2.17 (s, 3H); |
| | 3.78 (m, 2H); |
| | 3.89 (m, 2H); |
| | 5.74 (bs, 1H); |
| | 7.50 (m, 6H). |
| ¹³C NMR (CDCl₃, 100 MHZ): δ = | 22.63 (CH₃); |
| | 28.74 (CH₃); |
| | 39.41 (CH₂); |
| | 44.05 (CH₂); |
| | 51.70 (C); |
| | 116.98 (C); |
| | 124.19 (C); |
| | 128.20 (CH); |
| | 128 87 (CH); |
| | 131.43 (CH); |
| | 133.33 (CH); |
| | 163.00 (C = 0); |
| | 169.48 (C = 0); |
| | 171.51 (C = 0). |

EXAMPLE 11

1-Acetyl4-methoxycarbonyl-1,4,5,6-tetrahydropyrazine-2-carboxylic acid tert-butylamide Analogously to Example 9, the title compound was obtained in the form of a white crystalline solid from 1-acetyl-1,4,5,6-tetrahydropyrazine-2-carboxylic acid tert-butylamide and methyl chloroformate. The melting point of the title compound was: 134.0° to 135.3° C. Other data concerning the title compound was:

| | |
|---|---|
| ¹H NMR (CDCl₃, 400 MHZ): δ = | 1.40 (s, 9H); |
| | 2.12 (s, 3H); |
| | 3.67 (m, 4H); |
| | 3.84 (s, 3H); |
| | 5.70 (bs, 1H); |
| | 7.50 (bs, 1H). |
| ¹³C NMR (CDCl₃, 100 MHZ): δ = | 22.54 (CH₃); |
| | 28.77 (CH₃); |
| | 39.07 (CH₂); |
| | 44.05 (CH₂); |
| | 51.63 (C), |
| | 53.86 (CH₃) |
| | 116.32 (C); |
| | 122.48 (CH); |
| | 152.93 (C = 0); |
| | 163.26 (C = 0); |
| | 171.72 (C = 0). |

EXAMPLE 12
1-Acetyl4-phenoxycarbonyl-1,4,5,6-tetrahydropyrazine-2-carboxylic acid tert-butylamide Analogously to Example 9, the title compound was obtained in the form of a white crystalline solid from 1-acetyl-1,4,5,6-tetrahydropyrazine-2-carboxylic acid tert-butylamide and phenyl chloroformate. The melting point of the title compound was: 156.4° to 157.5° C. Other data concerning the title compound was:

| | |
|---|---|
| ¹H NMR (CDCl₃, 400 MHZ): δ = | 1.41 (s, 9H); |
| | 2.16 (s, 3H); |
| | 3.79 (m, 4H); |
| | 5.76 (bs, 1H); |
| | 7.13 to 7.41 (m, 6H). |
| ¹³C NMR (CDCl₃, 100 MHZ): δ = | 22.58 (CH₃), |
| | 28.74 (CH₃); |
| | 39.20 (CH₂); |
| | 44.27 (CH₂); |
| | 51.72 (C); |
| | 117.40 (C); |
| | 121.35 (CH); |
| | 126.23 (CH); |
| | 129.59 (CH); |
| | 150.59 (C); |
| | 150.9 (C = 0); |
| | 163.10 (C = 0); |
| | 171.60 (C = 0). |

EXAMPLE 13
1,4-Dipropionyl-1,4,5,6-tetrahydropyrazine-2-carboxylic acid tert-butylamide Analogously to Example 9, the title compound was obtained in the form of a white crystalline solid from 1-propionyl-1,4,5,6-tetrahydropyrazine-2-carboxylic acid tert-butylamide and propionyl chloride. The melting point of the title compound was: 131.0° to 132.8° C. Other data concerning the title compound was:

| | |
|---|---|
| ¹H NMR (CDCl₃, 400 MHz): δ = | 1.13 (t, J=7.3 Hz, 3H); |
| | 1.20 (t, J=7.3 Hz, 3H); |
| | 1.40 (s, 9H); |
| | 2.38 (q, J=7.3 Hz, 2H); |
| | 2.60 (q, J =7.3 Hz, 2H) |
| | 3.70 (m, 4H); |
| | 5.77 (bs, 1H), |
| | 7.39 (s, 1H). |
| ¹³C NMR (CDCl₃, 100 MHz): δ = | 8.81 (CH₃); |
| | 9.27 (CH₃); |
| | 26.68 (CH₂); |
| | 27.85 (CH₂); |
| | 28.76 (CH₃); |

-continued

| | |
|---|---|
| | 39.88 (CH₂) |
| | 42.67 (CH₂) |
| | 51.69 (C); |
| | 116.29 (C); |
| | 122.86 (CH); |
| | 163.29 (C=O); |
| | 171.93 (C=O); |
| | 175.49 (C=O). |

EXAMPLE 14
4-Acetyl-1-isobutyryl-1,4,5,6-tetrahydropyrazine-2-carboxylic acid tert-butylamide Analogously to Example 9, the title compound was obtained in the form of a white crystalline solid from 1-isobutyryl-1,4,5,6-tetrahydropyrazine-2-carboxylic acid tert-butylamide and acetyl chloride. The melting point of the title compound was: 116.3° to 117.2° C. Other data concerning the title compound was:

| | |
|---|---|
| ¹H NMR (CDCl₃, 400 MHz): δ = | 1.10 (d, J=6.6 Hz, 6H); |
| | 1.40 (s, 9H); |
| | 2.33 (s, 3H); |
| | 2.72 (m, 1H); |
| | 3.70 (m, 4H); |
| | 5.80 (bs, 1H); |
| | 7.37 (s, 1H). |
| ¹³C NMR (CDCl₃, 100 MHz): δ = | 19.33 (CH₃); |
| | 21.46 (CH₃); |
| | 28.67 (CH₃); |
| | 33.04 (CH); |
| | 39.81 (CH₂); |
| | 42.67 (CH₂); |
| | 51.65 (C); |
| | 116.17 (C); |
| | 123.49 (CH); |
| | 163.32 (C=O); |
| | 168.60 (C=O); |
| | 179.11 (C=O). |

EXAMPLE 15
1-Acetyl-4-methoxyacetyl-1,4,5,6-tetrahydropyrazine-2-carboxylic acid tert-butylamide Analogously to Example 9, the title compound was obtained in the form of a white crystalline solid from 1-acetyl-1,4,5,6-tetrahydropyrazine-2-carboxylic acid tert-butylamide and methoxyacetyl chloride. The melting point of the title compound was: 109.6° to 110.7° C. Other data concerning the title compound was:

| | |
|---|---|
| ¹H NMR (CDCl₃, 400 MHz): δ = | 1.41 (s, 9H); |
| | 2.14 (s, 3H); |
| | 3.46 (s, 3H); |
| | 3.73 (m, 4H); |
| | 4.32 (s, 2H); |
| | 5.73 (bs, 1H); |
| | 7.32 (s, 1H). |
| ¹³C NMR (CDCl₃, 100 MHz): δ = | 22.60 (CH₃); |
| | 28.76 (CH₃); |
| | 39.33 (CH₂); |
| | 42.67 (CH₂); |
| | 51.82 (C); |
| | 59.51 (CH₃); |
| | 71.31 (CH₂) |
| | 117.34 (C); |
| | 121.88 (CH); |
| | 162.89 (C=O); |
| | 167.26 (C=O); |
| | 171.62 (C=O). |

EXAMPLE 16
1-Propionyl-4-trifluoroacetyl-1,4,5,6-tetrahydropyrazine-2-carboxylic acid tert-butylamide Analogously to Example 9, the title compound was obtained in the form of a white crystalline solid from 1-propionyl-1,4,5,6-tetrahydropyrazine-2-carboxylic acid tert-butylamide and trifluoroacetyl chloride. The melting point of the title compound was: 132.6° to 133.3° C. Other data concerning the title compound was:

| | |
|---|---|
| $^1$H NMR($C_2D_2Cl_4$, 400 MHz, 100° C.): δ = | 1.13 (t, J=7 Hz, 3H); |
| | 1.38 (s, 9H); |
| | 2.35 (q, J=7.3 Hz, 2H); |
| | 3.80 (m, 4H); |
| | 5.66 (bs, 1H); |
| | 7.28 (bs, 1H) |
| $^{13}$C NMR ($C_2D_2Cl_4$, 100 MHz, 100° C.): δ = | |
| | 9.15 ($CH_3$); |
| | 27.86 ($CH_2$); |
| | 28.71 ($CH_3$); |
| | 40.10 ($CH_2$); |
| | 44.90 ($CH_2$); |
| | 51.88 (C); |
| | 115.87 (q, $^1J_{CF}$=286 Hz, $CF_3$); |
| | 117.75 (CH); |
| | 122.05 (C); |
| | 154.47 (q, $^2J_{CF}$=38.7 Hz, $COCF_3$); |
| | 162.17 (CONH); |
| | 173.96 (COEt). |

EXAMPLE 17
4-Formyl-1-propionyl-1,4,5,6-tetrahydropyrazine-2-carboxylic acid tert-butylamide Process A: Formylation with formyl chloride generated in situ 70.00 g (1.521 mol) of formic acid was added at 20° C. to a suspension of 70.00 g (0.293 mol) of 1-propionyl-1,4,5,6-tetrahydropyrazine-2-carboxylic acid tert-butylamide in 350 ml of butyl acetate. A solution of 63 g of thionyl chloride in 140 ml of butyl acetate was added dropwise over 4.5 hours to the yellowish solution obtained, the temperature being kept below 25° C. The reaction solution was washed with 50 ml of 5% sodium hydrogen carbonate solution and the aqueous phase was rewashed with 100 ml of dichloromethane. The two organic phases were combined and, after removal of the solvent, the residue was recrystallized from butyl acetate to give 71.2 g (82.7%) of the title compound in the form of a white crystalline solid.

Process B: Formylation with acetyl formyl anhydride [analogously to lit.:

J. C. Sheehan. D.-D. Yang. *J. Am. Chem. Soc.*, (1958). 80, 1154]

A mixture of 20.0 g (0.196 mol) of acetic anhydride and 18.00 g (0.391 mol) of formic acid was added dropwise over 30 minutes at 30° C to a solution of 31.2 g (0.13 mol) of 1-propionyl-1,4,5,6-tetrahydropyrazine-2-carboxylic acid tert-butylamide in 40.0 g (0.87 mol) of formic acid. The reaction mixture was stirred for a further 20 minutes at 30° C. 50 ml of water was then added and the clear solution was kept at 40° C. for 50 minutes. The product was extracted and crystallized from n-butyl acetate to give 30.75 g (88%) of the title compound in the form of a white crystalline solid. The melting point of the title compound was: 132.1° to 133.5° C. Other data concerning the title compound was:

| | |
|---|---|
| $^1$H NMR (CDCl$_3$, 400 MHz): δ = | 1.14 (t, J=7.3 Hz; 3H); |
| | 1.40 (s, 9H); |
| | 2.39 (q, J=7.3 Hz, 2H); |
| | 3.66 (m, 2H); |
| | 3.74 (m, 2H); |
| | 5.75 (bs, 1H); |
| | 7.22 (s, 1H); |
| | 8.41 (s, 1H). |
| $^{13}$C NMR (CDCl$_3$, 100 MHz): δ = | 9.25 ($CH_3$); |
| | 27.89 ($CH_2$); |
| | 28.67 ($CH_3$); |
| | 39.25 ($CH_2$); |
| | 45.06 ($CH_2$); |
| | 51.79 (C); |
| | 118.3 (C); |
| | 122.9 (CH); |
| | 161.01 (C=O); |
| | 162.79 (C=O); |
| | 175.4 (C=O). |

EXAMPLE 18

1-Acetyl-4-formyl-1,4,5,6-tetrahydropyrazine-2-carboxylic acid tert-butylamide

Analogously to Example 17 (Process B), the compound was obtained in the form of a white crystalline solid from 1-acetyl-1,4,5,6-tetrahydropyrazine-2-carboxylic acid tert-butylamide and Ac$_2$O/HCOOH. The melting point of the title compound was: 131.0° to 132.9° C. Other data concerning the title compound was:

| | |
|---|---|
| $^1$H NMR (CDCl$_3$, 400 MHz): δ = | 1.41 (s, 9H); |
| | 2.15 (s, 3H); |
| | 3.70 (m, 4H); |
| | 5.75 (bs, 1H); |
| | 7.21 (s, 1H); |
| | 8.41 (s, 1H). |
| $^{13}$C NMR (CDCl$_3$, 100 MHz): δ = | 22.62 ($CH_3$); |
| | 28.73 ($CH_3$); |
| | 38.65 ($CH_2$); |
| | 44.99 ($CH_2$); |
| | 51.85 (C); |
| | 118.27 (C); |

122.90 (CH);
160.94 (C=O);
162.63 (C=O);
171.7 (C=O).

EXAMPLE 19
(S)-1,4-Diacetylpiperazine-2-carboxylic acid tert-butylamide 10 g (37 mmol) of 1,4-diacetyl-1,4,5,6-tetrahydropyrazine-2-carboxylic acid tert-butylamide, 20.3 mg (37 μmol) of 1-[1(R)-(di-tert-butylphosphino)ethyl]-2(S)-(diphenylphosphino)ferrocene and 9.2 mg (20 μmol) of bicyclo[2.2.1]hepta-2,5-dienerhodium(I) chloride dimer were placed in an autoclave, oxygen being excluded. After flushing with argon, 80 ml of oxygen-free methanol was added. Hydrogenation was carried out at an initial pressure of 50 bar and a temperature of 110° C. for 20 hours. The autoclave was depressurized and flushed with nitrogen. The solvent of the reaction mixture was completely distilled off to give 10.50 g (95%) of the title product. GC analysis showed a conversion of 85 percent. After cleavage of the protecting groups with hydrochloric acid, the enantioselectivity of the hydrogenation was determined by GC analysis, giving an ee of 90.5 percent.

EXAMPLE 20
(S)-1,4-Diacetylpiperazine-2-carboxylic acid tert-butylamide 8.00 g (29.9 mmol) of 1,4-diacetyl-1,4,5,6-tetrahydropyrazine-2-carboxylic acid tert-butylamide, 10.0 mg (18 μmol) of 1-[1(R)-(di-tert-butylphosphino)-ethyl]-2(S)-(diphenylphosphino)ferrocene and 6.0 mg (16 μmol) of bis(bicyclo[2.2.1]hepta-2,5-diene)rhodium(I) tetrafluoroborate were placed in an autoclave, oxygen being excluded. After flushing with argon, 80 ml of oxygen-free methanol was added. Hydrogenation was carried out at an initial pressure of 50 bar and a temperature of 110° C. for 20 hours. Working-up of the reaction mixture analogously to Example 19 gave 10.50 g (75%) of the title product. GC analysis showed a conversion of 97 percent. After cleavage of the protecting groups with hydrochloric acid, the enantioselectivity of the hydrogenation was determined by GC analysis, giving an ee of 90.7 percent. The melting point of the title compound was: 139.9° to 150.6° C. Other data concerning the title compound was:

$^1$H NMR (CDCl$_3$, 400 MHZ): δ = 1.31; 1.33 (2s, 9H);
2.10; 2.12; 2.15; 2.17; 2.19; 2.22;
2.26 (7s, 6H);
2.77 to 2.83 (m, 1H);
3.18 to 3.28 (m, 2H);
3.70 to 3.73 (m, 1H);
4.41 to 4.49 (m, 2H);
5.04 (bs, 1H);
5.95 (bs, 1H).

EXAMPLE 21
(S)-4-Formyl-1-propionylpiperazine-2-carboxylic acid tert-butylamide 16.1 g (60.2 mmol) of 4-formyl-1-propionyl-1,4,5,6-tetrahydropyrazine-2-carboxylic acid tert-butylamide, 19.5 mg (35.9 μmol) of 1-[1(R)-(di-tert-butylphosphino)-ethyl]-2(S)-(diphenylphosphino)ferrocene and 11.1 mg (29.6 μmol) of bis(bicyclo[2.2.1]hepta-2,5-diene)rhodium(I) tetrafluoroborate were placed in an autoclave, oxygen being excluded. After flushing with argon, 80 ml of oxygen-free methanol was added. Hydrogenation was carried out at an initial pressure of 12 bar and a temperature of 90° C. for 8 hours. The autoclave was depressurized and flushed with nitrogen. The solvent of the reaction mixture was completely distilled off to give 17.00 g (94%) of the title product. GC analysis showed a conversion of 99 percent. After cleavage of the protecting groups with hydrochloric acid, the enantioselectivity of the hydrogenation was determined by GC analysis, giving an ee of 96.5 percent. The melting point of the title compound was: 132.1° to 134.3° C. Other data concerning the title compound was:

$^1$H NMR(CDCl$_3$, 400MHz): δ = 1.21(t, J=7.3Hz, 3H);
1.30; 1.31(2s, 9H);
2.46(q, J=7.3Hz, 2H);
2.75 to 2.82(m, 1H);
3.12 to 3.18(m, 2H);
3.60 to 3.78(m, 1H);
4.21 to 4.38(m, 2H);
5.07(bs, 1H);
5.92(bs, 1H);
8.10; 8.18(2s, 1H).

EXAMPLES 22 to 41

Analogously to Example 19, various tetrahydropyrazine derivatives II were hydrogenated in methanol in the presence of 1-[1-(R)-(di-tert-butylphosphino) ethyl]-2-(S)-(diphenylphosphino)ferrocene and [Rh(cod)Cl]$_2$ (A) or Rh(nbd)$_2$BF$_4$ (B) (cod=1,5-cyclooctadiene, nbd=bicyclo [2.2.1]heptadiene). The results are collated in Table 1 below. The following information is indicated for each Example: the molar ratio educt: rhodium, the substituents X, R$^1$ and R$^2$, the reaction conditions, the catalyst used, the conversion and the enantiomeric excess (ee).

The (S) enantiomer was the preferential product formed in each case.

TABLE 1

| Educt:Rh | X/R$^1$/R$^2$ | Temp [° C.]/Time [h] | Pressure [bar] | Catalyst | Conversion [%] | ee [%] |
|---|---|---|---|---|---|---|
| 500 | NH-t-Bu/Ac/Ac | 90/4 | 50 | B | 94 | 93.7 |
| 1000 | NH-t-Bu/EtCO/EtCO | 90/22 | 50 | B | 91 | 87.5 |
| 1000 | NH-t-Bu/EtCO/Ac | 90/22 | 10 | B | 94 | 91 |

TABLE 1-continued

| Educt:Rh | X/R$^1$/R$^2$ | Temp [° C.]/Time [h] | Pressure [bar] | Catalyst | Conversion [%] | ee [%] |
|---|---|---|---|---|---|---|
| 1000 | NH-t-Bu/Ac/COPh | 90/21 | 50 | B | 83 | 89.9 |
| 475 | NH-t-Bu/Me$_2$CHCO/Ac | 90/21 | 50 | B | 96.9 | 86.3 |
| 1000 | NH-t-Bu/Ac/COOMe | 90/20 | 50 | B | 97 | 88.3 |
| 480 | NH-t-Bu/Ac/CHO | 90/1 | 50 | B | 99.8 | 96.9 |
| 487 | NH-t-Bu/EtCO/CHO) | 90/2 | 50 | B | 99.7 | 96.5 |
| 482 | NH-t-Bu/EtCO/CHO | 70/6 | 12 | B | 99.8 | 96.8 |
| 475 | NH-t-Bu/CHO/CHO | 70/6 | 12 | B | 72.4 | 91.7 |
| 400 | NH-t-Bu/EtCO/COCF$_3$ | 90/17 | 50 | B | 95 | 88.2 |
| 400 | NH-t-Bu/Ac/MeOCH$_2$CO | 70/6 | 12 | B | 99 | 84.5 |
| 250 | NH-t-Bu/Ac/H | 70/20 | 50 | A | 87 | 58 |
| 500 | NH-t-Bu/EtCO/H | 90/24 | 50 | A | 78 | 52 |
| 500 | NH-t-Bu/COCHMe$_2$/H | 90/23 | 50 | B | 74 | 41 |
| 500 | NH-t-Bu/COCH$_2$OMe/H | 90/23 | 50 | B | 39 | 56 |
| 25 | OMe/H/H | 50/20 | 50 | A | 87 | 40 |
| 250 | OMe/Ac/H | 70/20 | 50 | A | 87 | 58 |
| 500 | OMe/Ac/H | 70/22 | 50 | A | 59 | 37.8 |
| 245 | OMe/Ac/Ac | 50/20 | 50 | A | 74 | 95 |

EXAMPLE 42

1-Trifluoroacetyl-1,4,5,6-tetrahydropyrazine-2-carboxylic acid tert-butylamide 50 ml of trifluoroacetic acid was placed in a 500 ml flask under argon. 12.5 g of methanesulfonic acid was added dropwise at 21° C. and 20 g of 2-cyano-1,4,5,6-tetrahydropyrazine methanesulfonic acid salt (97 mmol) was then added in portions, a slight exothermicity being observed. 10 g (178 mmol) of isobutane was then introduced over 1 hour at 20° C. The reaction mixture was stirred for a further 2 hours at 20° C., 13.3 g (111 mmol) of thionyl chloride was then added dropwise at this temperature and stirring was continued for a further 20 hours. 250 ml of dichloromethane was then added, followed by 25 g of sodium acetate in portions. After filtration of the crude solution through Celite®, 30 ml of water was added and the phases were separated. The organic phase was concentrated to dryness. The residual crude product (27.88 g) was chromatographed with ethyl acetate/methanol (4:1) on 300 g of silica gel. The yield (GC) was 29.2 percent. The melting point of the title compound was: 158° to 160° C. (from n-butyl acetate). Other data concerning the title compound was:

| | |
|---|---|
| $^1$H NMR(CDCl$_3$ 400MHz): δ = | 1.35(s, 9H); |
| | 3.43(bs, 2H); |
| | 3.74(bs, 2H); |
| | 5.32(bs, 1H); |
| | 5.53(bs, 1H); |
| | 7.06(d, J=6Hz, 1H). |
| $^{13}$C NMR(CDCl$_3$ 100MHz): δ = | 28.9; |
| | 42.3; |
| | 42.8; |
| | 51.2; |
| | 105.9; |
| | 116.3($^1$J$_{CF}$=288Hz); |
| | 133.2; |
| | 154.5($^2$J$_{CF}$=35Hz); |
| | 163.7. |

EXAMPLE 43

4-Formyl-1-trifluoroacetyl-1,4,5,6-tetrahydropyrazine-2-carboxylic acid tert-butylamide.

49.60 g (416.9 mmol) of thionyl chloride was added over 40 min at 20° C. to a solution of 96.94 g (347.1 mmol) of 1-trifluoroacetyl-1,4,5,6-tetrahydropyrazine-2-carboxylic acid tert-butylamide in 465.9 g (10.1 mol) of formic acid. After a reaction time of 2 hours at 20° C., the mixture was concentrated on a rotary evaporator at 60° C. and 80 mbar and the brownish-black residue was taken up with 400 ml of ethyl acetate and 400 ml of water. The aqueous phase was washed again with twice 250 ml of ethyl acetate and the combined organic extracts were dried over 50.1 g of sodium sulfate. After filtration, the solution was concentrated on a rotary evaporator and the viscous residue was stirred with 250 ml of diisopropyl ether. The precipitated solid was filtered off, washed with twice 100 ml of diisopropyl ether and dried. The yield was 96.76 g (91 %) of colorless crystals. The melting point of the title compound was: 158.4° to 160.3° C. Other data concerning the title compound was:

NMR data: One or a double set of signals are visible in the $^1$H and $^{13}$C NMR. Where an assignment was possible, the signals of the major conformer are labeled with *.

| | |
|---|---|
| $^1$H NMR(CDCl$_3$, 400MHz): δ = | 8.40(s, 1H)*; |
| | 8.14(s, 1H); |
| | 7.41(s, 1H); |
| | 7.14(s, 1H); |
| | 5.65(bs, 1H); |
| | 5.55(bs, 1H)*; |
| | 3.93–3.80(m, 2x4H); |
| | 1.40(s, 9H); |
| | 1.39(s, 9H)*. |
| $^{13}$C NMR(CDCl$_3$, 100MHz): δ = | 161.69; |
| | 161.14; |
| | 160.49; |
| | 159.61; |
| | 122.76; |
| | 119.76; |
| | 117.42; |
| | 115.84($^1$J$_{CF}$=288Hz); |
| | 52.04; |
| | 52.00; |
| | 44.77; |
| | 41.83; |
| | 41.11; |
| | 28.62. |

EXAMPLE 44

(S)-4-Formyl-1-(trifluoroacetyl)piperazine-2-carboxylic acid tert-butylamide 20.6 g (67.0 mmol) of 4-formyl-1-trifluoroacetyl-1,4,5,6-tetrahydropyrazine-2-carboxylic acid tert-butylamide, 26.2 mg (64.5 μmol) of bis(1,5-cyclooctadiene)rhodium(I) tetrafluoroborate and 41.8 mg (77 μmol) of 1-[1(R)-(di-tert-butylphospino)ethyl]-2-(S)-(diphenylphosphino)-ferrocene were placed in a 160 ml autoclave under argon (S/C=1000). 70 ml of acetone (degassed) was added and hydrogenation was carried out for 11 hours at 100° C. under a hydrogen pressure of 13–10 bar. After distillation of the solvent, 20.5 g (99%) of the title compound was obtained in the form of a crystalline solid. After cleavage of the protecting groups, the enantioselectivity of the hydrogenation was determined by GC analysis, giving an ee of 96.4 percent. The melting point of the title compound was: 172.0° to 173.0° C. Other data concerning the title compound was:

$^1$H NMR(DMSO-d$_6$, 400MHz, 70° C): δ = 8.06 and 8.02(2s, 1H); 7.63(b"d[, 1H); 4.90–2.95(m, 7H); 1.28 and 1.23(2s, 9H).
$^{13}$C NMR(DMSO-d$_6$, 100MHz, 70° C.)
Selected signals: δ = 166.94; 166.70; 161.05; 160.94; 156.22(q, $^2J_{CF}$=35Hz, COCF$_3$); 116.32(q, $^1J_{CF}$=288Hz, CF$_3$).

EXAMPLE 45
(S)-1-(Trifluoroacetyl)piperazine-2-carboxylic acid tert-butylamide sulfuric acid salt (1:1)

2.50 g (8.95 μmol) of 1-trifluoroacetyl-1,4,5,6-tetrahydropyrazine-2-carboxylic acid tert-butylamide, 7.5 mg (18 μmol) of bis(1,5-cyclooctadiene)rhodium(I) tetrafluoroborate and 11.5 mg (21 μmol) of 1-[1(R)-(di-tert-butylphosphino)ethyl]-2-(S)-(diphenylphosphino)ferrocene were placed in a 50 ml autoclave under argon (educt:catalyst=486). A solution of 0.89 g (9.08 mmol) of sulfuric acid in 20 ml of degassed tetrahydrofuran was then added. Hydrogenation was then carried out for 18 hours at 200° C. under a hydrogen pressure of 13–10 bar. After distillation of the solvent, 3.42 g (>99%) of the title compound were obtained in the form of a white powder. After cleavage of the protecting groups, the enantioselectivity of the hydrogenation was determined by GC analysis, giving an ee of 79.5 percent. Other data concerning the title compound was:

$^1$H NMR(DMSO-d$_6$, 400MHz): δ = 9.60–8.30(m, 2H); 7.88(bs, 1H); 4.95–3.05(m, 7H); 1.32(s, 9H).
$^{13}$C NMR(DMSO-d$_6$, 100MHz)
Selected signals: δ = 166.94(CONH); 115.90(q, $^1J_{CF}$=288Hz, CF$_3$).

EXAMPLE 46
(S)-1-(Trifluoroacetyl)piperazine-2-carboxylic acid tert-butylamide 250 g (8.95 mmol) of 1-trifluoroacetyl-1,4,5,6-tetrahydropyrazine-2-carboxylic acid tert-butylamide, 7.5 mg (18 μmol) of bis(1,5-cyclooctadiene)rhodium(I) tetrafluoroborate and 11.5 mg (21 μmol) of 1-[1(R)-(di-tert-butylphosphino)ethyl]-2(S)-(diphenylphosphino)ferrocene were placed in a 50 ml autoclave under argon (educt:catalyst=486). 20 ml of degassed ethyl acetate was added and hydrogenation was carried out for 18 hours at 90° C. under a hydrogen pressure of 13–10 bar. After distillation of the solvent, 2.50 g of the crude title compound was obtained in the form of a light yellow powder. After cleavage of the protecting groups, the enantioselectivity of the hydrogenation was determined by GC analysis, giving an ee of 47.2 percent. Other data concerning the title compound was:

$^1$H NMR(CDCl$_3$, 400MHz)(Only the signals of the major isomer are given.) δ = 5.88(bs, 1H); 4.68–4.65("d", 1H); 3.85–3.78("d", 1H); 3.54–3.49("d", 1H); 3.41–3.32("dt", 1H); 3.11–3.06("d", 1H); 2.90–2.78(m, 2H); 2.07(s, 1H); 1.34(s, 9H).

EXAMPLE 47
(S)-1-(Trifluoroacetyl)piperazine-2-carboxylic acid tert-butylamide BF$_3$ adduct 2.50 g (8.95 mmol) of 1-trifluoroacetyl-1,4,5,6-tetrahydropyrazine-2-carboxylic acid tert-butylamide, 7.5 mg (18 μmol) of bis(1,5-cyclooctadiene)rhodium(I) tetrafluoroborate and 11.5 mg (21 μmol) of 1-[1(R)-(di-tert-butylphosphino)ethyl]-2(S)-(diphenylphosphino)ferrocene were placed in a 50 ml autoclave under argon (educt:catalyst=488). A solution of 0.71 g (6.83 mmol) of boron trifluoride dihydrate in 20 ml of degassed tetrahydrofuran was added. Hydrogenation was then carried out for 18 hours at 90° C. under a hydrogen pressure of 13–10 bar. After distillation of the solvent, 3.09 g of the crude title compound was obtained in the form of a white powder. After cleavage of the protecting groups, the enantioselectivity of the hydrogenation was determined by GC analysis, giving an ee of 51.6 percent.

EXAMPLE 48
(S)-4-Formylpiperazine-2-carboxylic acid tert-butylamide

A solution of 25.5 g (184.5 mmol) of potassium carbonate in 130 ml of water was added to 15.0 g (48.5 mmol) of (S)-4-formyl-1-(trifluoroacetyl)-piperazine-2-carboxylic acid tert-butylamide in 130 ml of isobutyl alcohol and the mixture was heated at 60° to 65° C. for 1 hour. After phase separation, the aqueous phase was extracted with 100 ml of isobutyl alcohol and the combined organic phases were evaporated to give 14.10 g of the crude title compound (still containing solvent) in the form of a light yellow oil. Other data concerning the title compound was:

MS: m/z=213 (M$^+$, 1%), 198 (1%), 155 (2%), 113 (100%), 85 (36%), 56 (89%).

$^1$H NMR(CDCl$_3$, 400MHz): δ = 8.06 and 8.04(2bs, 1H); 6.86 and 6.47(2bs, 1H); 4.32 to 4.27 and 3.76 to 3.61(3m, 2H); 3.48 to 3.41("dd", 1 H); 3.28 to 3.15(m, 2H); 3.07 to 2.90(m, 1H); 2.80 to 2.71(m, 1H); 1.35(s, 9H).

EXAMPLE 49
(S)4-Formylpiperazine-2-carboxylic acid tert-butylamide acetic acid salt (1:1)

120 ml of acetic acid was added to 21.58 g (101.2 mmol) of (S)-4-formylpiperazine-2-carboxylic acid tert-butylamide in 120 ml of tetrahydrofuran and the mixture was evaporated to dryness. 100 ml of toluene was then added and the mixture was concentrated on a rotary evaporator. After the addition of 100 ml of 1,4-dioxane, the mixture was concentrated again and a solid precipitated out. The residue was suspended in 150 ml of ethyl acetate and filtered off. After washing with ethyl acetate and diethyl ether and drying, 20.10 g (73%) of the title compound was obtained in the form of a white crystalline solid. Other data concerning the title compound was:

| $^1$H NMR(DMSO-d$_6$, 400MHz): δ = | 8.00 and 7.98(2s, 1H); |
| --- | --- |
| | 7.37 and 7.33(2bs, 1H); |
| | 4.09 to 4.03 and 3.68 to |
| | 3.43(4"d", 2H); |
| | 3.21 to 3.11(m, 1H); |
| | 3.08 to 2.99(m, 1 H); |
| | 2.96 to 2.87(m, 1 H); |
| | 2.83 to 2.76 and |
| | 2.70 to 2.61(2m, 1H); |
| | 2.59 to 2.46(m; 1 H); |
| | 1.91(s, 3H); |
| | 1.26(s, 9H). |

EXAMPLE 50

(S)-1-(Trifluoroacetyl)piperazine-2-carboxylic acid tert-butylamide

A mixture of 50.5 g (430 mmol) of 32% hydrochloric acid and 50 ml of water was added to 32.0 g (103 mmol) of (S)-4-formyl-1-(trifluoroacetyl) piperazine-2-carboxylic acid tert-butylamide in 200 ml of acetone and the resulting mixture was heated at 60° to 65° C. for 2.5 hours. After cooling to 20° C., neutralization was carried out with triethylamine in such a way that the temperature remained below 30° C. The solvent was evaporated off, and 100 ml of water and 200 ml of methyl isobutyl ketone were added. At 50° C. the phases were separated and the aqueous phase was re-extracted with twice 100 ml of methyl isobutyl ketone. The combined organic extracts were dried over magnesium sulfate and evaporated to dryness to give 23.5 g (80%) of the title compound in the form of a slightly reddish solid. Recrystallization from toluene/diisopropyl ether gave the title compound in the form of a white crystalline powder. The melting point of the title compound was: 143.5° to 144.2° C. Other data concerning the title compound was:

| $^1$H NMR(CDCl$_3$, 400MHz)(Only the signals of the major isomer are given.) δ = | 5.88(bs, 1H); |
| --- | --- |
| | 4.68 to 4.65("d", 1H); |
| | 3.85 to 3.78("d", 1H); |
| | 3.54 to 3.49("d", 1H); |
| | 3.41 to 3.32("dt", 1H); |
| | 3.11 to 3.06("d", 1H); |
| | 2.90 to 2.78(m, 2H); |
| | 2.07(s, 1H); |
| | 1.34(s, 9H). |

EXAMPLE 51

(S)-3-(tert-Butylcarbamoyl)piperazine-1-carboxylic acid tert-butyl ester [=(S)-4-(tert-butoxycarbonyl)piperazine-2-carboxylic acid tert-butylamide]

The reaction mixture resulting from the asymmetric hydrogenation of 50.0 g (162.7 mmol) of 4-formyl-1-trifluoroacetyl-1,4,5,6-tetrahydropyrazine-2-carboxylic acid tert-butylamide was placed in a 1 l jacketed stirring vessel, a mixture of 64.75 g (567 mmol) of 32% hydrochloric acid and 130 g of water was added and the reaction mixture was refluxed (ca. 60° C.) for 2 hours. It was cooled to 20° C. and 73.76 g (729 mmol) of triethylamine was added in such a way that the temperature did not exceed 30° C. A solution of 31.82 g (145.8 mmol) of di-tert-butyl dicarbonate in 35 g of acetone was then added over 1 hour at 30° C. After a post-reaction time of 15 min, the acetone was distilled off at a maximum of 40° C. and 100 mbar. 300 ml of methanol and a solution of 45.36 g (1.13 mol) of sodium hydroxide in 65 g of water were added to the residue, the mixture was refluxed for 2 hours, and the excess methanol was then distilled off at a maximum of 48° C. and 100 mbar. 100 ml of water and 200 ml of methylcyclohexane were then added, the mixture was heated at 55° C. for 5 min and the phases were separated. The aqueous phase was washed again with twice 75 ml of methylcyclohexane at 55° C. and the combined organic phases were partially evaporated at 50° to 60° C., causing crystallization to begin. The mixture was then cooled to 15° C. and the temperature was maintained for 1 hour. After a further hour at 0° C., the mixture was filtered and the residue was washed with 100 ml of cold diisopropyl ether. After drying, 35.45 g (77%) of the title compound was obtained in the form of a white crystalline solid. After cleavage of the protecting groups, the enantioselectivity of the hydrogenation was determined by GC analysis, giving an ee of 98.7 percent. Other data concerning the title compound was:

| $^1$H NMR(400MHz, CDCl$_3$): δ = | 6.75 to 6.45(bs, 1H); |
| --- | --- |
| | 4.13 to 4.02(m, 1H); |
| | 3.90 to 3.70(bs, 1H); |
| | 3.20(dd, J=3.7, 9.3Hz, 1H); |
| | 3.02 to 2.80(m, 3H); |
| | 2.80 to 2.70(m, 1H); |
| | 2.05 to 1.90(bs, 1H); |
| | 1.47(s, 9H); |
| | 1.35(s, 9H). |
| $^{13}$C NMR(100MHz, CDCl$_3$): δ = | 170.27; |
| | 154.76; |
| | 80.11; |
| | 58.93; |
| | 50.93; |
| | 43.40; |
| | 44.17; |
| | 44.00; |
| | 28.75; |
| | 28.43. |

What is claimed is:

1. A process for the preparation of an optically active piperazine-2-carboxylic acid derivative of formula:

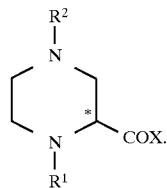

wherein $R^1$ and $R^2$ independently of one another are each hydrogen, $C_{1-4}$-alkyl, $C_{1-6}$-alkanoyl, $C_{1-6}$-alkanoyl substituted with at least one $C_{1-4}$-alkoxy, $C_{2-6}$-perfluoroalkanoyl, aroyl, arylalkyl, $C_{1-6}$-alkoxycarbonyl, aryloxycarbonyl, carbamoyl or an amino-protecting group, and X is a hydroxyl group, a $C_{1-6}$-alkoxy group or a group of the formula $NR^3R^4$, wherein (i) $R^3$ and $R^4$ independently of one another are hydrogen, $C_{1-6}$-alkyl, $C_{3-6}$-cycloalkyl, aryl or an amino-protecting group, or (ii) $R^3$ and $R^4$, together with the nitrogen atom, form a morpholino ring, or (iii) $R^3$ is hydrogen and $R^4$ is a group of formula:

wherein $R^6$ is hydrogen, $C_{1-4}$-alkyl or aryl and $R^5$ is hydrogen or a side group of a natural amino acid, comprising asymmetrically hydrogenating a corresponding 1,4,5,6-tetrahydropyrazine-2-carboxylic acid derivative or formula:

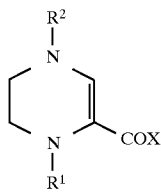

wherein $R^1$, $R^2$ and X are as define above, in the presence of a catalytically active, optically active rhodium complex formed from an Rh(I) complex and an optically active metalocenylphosphine, the optically active metallocenylphosphine being a compound of the general formula:

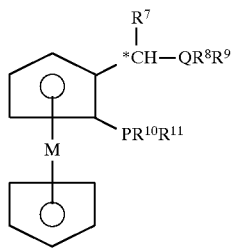

wherein M is iron(II) or ruthenium(II), Q is nitrogen or phosphorus, $R^7$ is a $C_{1-4}$-alkyl group and $R^8$ to $R^{11}$ independently of one another are $C_{1-8}$-alkyl, $C_{5-8}$-cycloalkyl, phenyl or substituted phenyl.

2. The process according to claim 1, wherein M is iron(II).

3. The process according to claim 2, wherein Q is phosphorus.

4. The process according to claim 3, wherein $R^7$ is methyl and $R^8$ and $R^9$ are identical and are tert-butyl or cyclohexyl.

5. The process according to claim 4, wherein the Rh(I) complex used is a neutral complex of formula:

wherein L is one $C_{4-12}$-diene or two $C_{2-12}$-alkene molecules and A is chlorine, bromine or iodine.

6. The process according to claim 4, wherein the Rh(I) complex used is a cationic complex of the general formula:

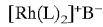

wherein L is one $C_{4-12}$-diene or two $C_{2-12}$-alkene molecules and $B^-$ is the anion of an oxo acid or a complex acid.

7. The process according to claim 5, wherein L is norbornadiene or 1,5-cyclooctadiene.

8. The process according to claim 6, wherein L is norbornadiene or 1,5-cyclooctadiene.

9. The process according to claim 1, wherein the 1,4,5,6-tetrahydropyrazine-2-carboxylic acid derivative II used is a compound in which $R^1$ and/or $R^2$ are each $C_6$-alkanoyl, $C_{2-6}$-perfluoroalkanoyl, tert-butoxycarbonyl or benzyloxycarbonyl.

10. The process according to claim 9, wherein the 1,4,5,6-tetrahydropyrazine-2-carboxylic acid derivative II used is an amide in which X is a group of the formula $-NR^3R^4$.

11. The process according to claim 10, wherein $R^3$ is hydrogen and $R^4$ is a $C_{1-6}$-alkyl group.

12. The process according to claim 11, wherein $R^4$ is a tert-butyl group.

13. The process according to claim 1, wherein the 1,4,5,6-tetrahydropyrazine-2-carboxylic acid derivative II used is an amide in which X is a group of the formula $-NR^3R^4$.

14. A process for the preparation of an optically active piperazine-2-carboxylic acid derivative of formula:

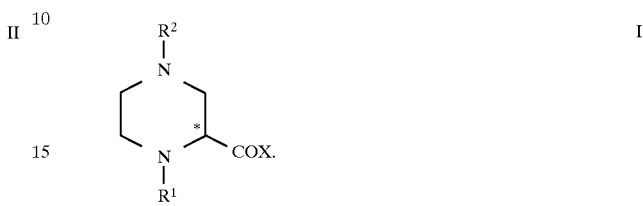

wherein $R^1$ and $R^2$ independently of one another are each hydrogen, $C_{1-4}$-alkyl, $C_{1-6}$-alkanoyl, arylalkyl, $C_{1-6}$-alkoxycarbonyl, carbamoyl or an amino-protecting group, and X is a hydroxyl group, a $C_{1-6}$-alkoxy group or a group of the formula $-NR^3R^4$, wherein (i) $R^3$ and $R^4$ independently of one another are hydrogen, $C_{1-6}$-alkyl, $C_{3-6}$-cycloalkyl, aryl or an amino-protecting group, or (ii) $R^3$ and $R^4$, together with the nitrogen atom, form a morpholino ring, or (iii) $R^3$ is hydrogen and $R^4$ is a group of formula:

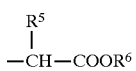

wherein $R^6$ is hydrogen or $C_{1-6}$-alkoxy and $R^5$ is hydrogen or a side-group of a natural amino acid, characterized in that a corresponding 1,4,5,6-tetrahydropyrazine-2-carboxylic acid derivative of formula:

wherein $R^1$, $R^2$ and X are as defined above, is asymmetrically hydrogenated in the presence of a catalytically active, optically active rhodium complex, the optically active rhodium complex being a complex formed from an Rh(I) complex and an optically active metallocenylphosphine, the optically active metallocenylphosphine being a compound of formula:

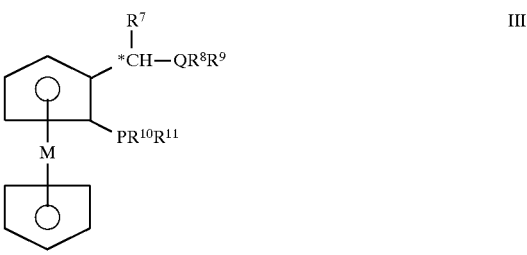

wherein M is iron(II) or ruthenium(II), Q is nitrogen or phosphorus, $R^7$ is a $C_{1-4}$-alkyl group and $R^8$ and $R^9$ independently of one another are $C_{1-8}$-alkyl, $C_{5-8}$-cycloalkyl, phenyl or substituted phenyl.

15. A process according to claim 14, wherein M is iron(II).

16. A process according to claim 14, wherein Q is phosphorus.

17. A process according to claim 14, wherein $R^7$ is methyl and $R^8$ and $R^9$ are identical and are tert-butyl or cyclohexyl.

18. A process according to claim 17, wherein the Rh(I) complex used is a neutral complex of formula:

$$[\text{Rh (L)A}]_2 \quad \quad \text{IV}$$

wherein L is one $C_{1-4}$-diene or two $C_{2-12}$-alkene molecules and A is chlorine, bromine or iodine.

19. A process according to claim 17, wherein the Rh(I) complex used is a cationic complex of formula:

$$[\text{Rh (L)}_2]^+ \text{B}^- \quad \quad \text{V}$$

wherein L is one $C_{4-12}$-diene or two $C_{2-12}$-alkene molecules and $B^-$ is the anion of an oxo acid or complex acid.

20. A process according to claim 19, wherein L is norbornadiene or 1,5-cyclooctadiene.

21. The process according to claim 14, wherein the 1,4,5,6-tetrahydropyrazine-2-carboxylic acid derivative II used is a compound in which $R^1$ and/or $R^2$ are each $C_{1-6}$-alkanoyl, $C_{2-6}$-perfluoroalkanoyl, tert-butoxycarbonyl or benzyloxycarbonyl.

22. The process according to claim 21, wherein the 1,4,5,6-tetrahydropyrazine-2-carboxylic acid derivative II used is an amide in which X is a group of the formula —$NR^3R^4$.

23. The process according to claim 22, wherein $R^3$ is hydrogen and $R^4$ is a $C_{1-6}$-alkyl group.

24. The process according to claim 23, wherein $R^4$ is a tert-butyl group.

25. A process according to claim 14, wherein the 1,4,5,6-tetrahydropyrazine-2-carboxylic acid derivative II used is an amide in which X is a group of the formula —$NR^3R^4$.

* * * * *